United States Patent
DeMayo

(10) Patent No.: US 10,617,404 B2
(45) Date of Patent: *Apr. 14, 2020

(54) MODULAR DISTRACTOR SYSTEM FOR USE IN SURGERY

(71) Applicant: INNOVATIVE MEDICAL PRODUCTS, INC., Plainville, CT (US)

(72) Inventor: Edward DeMayo, Greenbrae, CA (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 201 days.

This patent is subject to a terminal disclaimer.

(21) Appl. No.: 15/098,609

(22) Filed: Apr. 14, 2016

(65) Prior Publication Data
US 2016/0228114 A1 Aug. 11, 2016

Related U.S. Application Data

(63) Continuation of application No. 13/134,238, filed on Jun. 3, 2011, now Pat. No. 9,314,272.

(51) Int. Cl.
| | |
|---|---|
| A61B 17/02 | (2006.01) |
| A61B 17/66 | (2006.01) |
| A61G 13/00 | (2006.01) |
| A61F 5/04 | (2006.01) |
| A61G 13/10 | (2006.01) |
| A61G 13/12 | (2006.01) |
| A61B 17/60 | (2006.01) |
| A61B 17/68 | (2006.01) |

(52) U.S. Cl.
CPC ............ *A61B 17/025* (2013.01); *A61B 17/66* (2013.01); *A61F 5/04* (2013.01); *A61G 13/0036* (2013.01); *A61G 13/101* (2013.01); *A61G 13/1245* (2013.01); *A61B 17/60* (2013.01); *A61B 2017/681* (2013.01)

(58) Field of Classification Search
CPC . A61B 17/66; A61B 2017/681; A61B 17/025; A61B 2017/0268; A61B 2017/0275; A61B 17/60
See application file for complete search history.

(56) References Cited

U.S. PATENT DOCUMENTS

| | | | | |
|---|---|---|---|---|
| 3,020,909 A | * | 2/1962 | Stevens ............... | A61G 13/0036 5/623 |
| 4,526,355 A | * | 7/1985 | Moore ............... | A61G 13/0063 5/624 |
| 5,020,525 A | * | 6/1991 | Ewing ....................... | A61F 5/04 602/27 |
| 5,025,802 A | * | 6/1991 | Laico ..................... | A61G 13/12 128/875 |
| 5,290,220 A | * | 3/1994 | Guhl ........................ | A61F 5/04 128/882 |

* cited by examiner

*Primary Examiner* — Anu Ramana
(74) *Attorney, Agent, or Firm* — Damian Wasserbauer, Esq.; Wasserbauer Law LLC

(57) ABSTRACT

A manual distractor unit is mounted upon a support frame attached to an operating table side rail. An ankle strap is attached to the support frame and to the patient's ankle. A patient's knee support pad, extending from the distractor unit, is positioned under the patient's knee to provide traction to the patient's limb at the ankle, which is secured to the support frame by the ankle strap.

3 Claims, 2 Drawing Sheets

MODULAR DISTRACTOR SYSTEM FOR USE IN SURGERY

CROSS-REFERENCE TO RELATED APPLICATION

This application is a continuation of and claims the benefit of U.S. patent application Ser. No. 13/134,238 filed Jun. 3, 2011 entitled "Modular distractor for use in ankle surgery" which is incorporated by reference herein in its entirety. The patent application identified above is incorporated here by reference in its entirety to provide continuity of disclosure.

FIELD OF THE INVENTION

The present invention relates to ankle distraction procedures and, more particularly, to an apparatus, system and method for distracting an ankle and/or leg at a knee to provide improved access to the ankle area and lower leg.

BACKGROUND OF THE INVENTION

Methods currently available for ankle distraction procedures generally restrain the patient's leg and apply controlled pressure to the ankle for the required traction.

U.S. Pat. No. 5,290,220 entitled "Non-Invasive Distraction System for Ankle Arthroscopy" and U.S. Pat. No. 5,025,802 entitled "Surgical Holding Apparatus for Distracting Ankle" both describe applying such traction to the ankle directly.

The use of such equipment in the vicinity of the ankle could impair circumferential access to the patient's foot and ankle, during surgery, under some circumstances.

It has been shown that by restraining the patient's ankle with a simple strap and applying pressure to the underside of the patient's knee, the ankle can be distracted while allowing the surgeon complete access to the ankle in all directions.

One purpose of the instant invention is to provide a simple means of securing the patient's ankle while applying pressure to the underside of the patient's knee for such ankle arthroscopy by means of a manual distractor which can also be used for other joint arthroscopic surgery.

SUMMARY OF THE INVENTION

One end of a manual distractor unit used in various joint distraction surgery is mounted to one end of a support frame attached to an operating table side rail. A patient's knee support pad, at an opposite end of the distractor unit, is positioned under the patient's knee to provide traction to the patient's ankle, which is secured by a strap to the support frame.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Preferred Embodiment, which is to be read in association with the accompanying drawings, which are incorporated in and constitute a part of this specification, show certain aspects of the subject matter disclosed herein and, together with the description, help explain some of the principles associated with the disclosed implementations, wherein.

DESCRIPTION OF THE PREFERRED EMBODIMENTS

Figure 1:
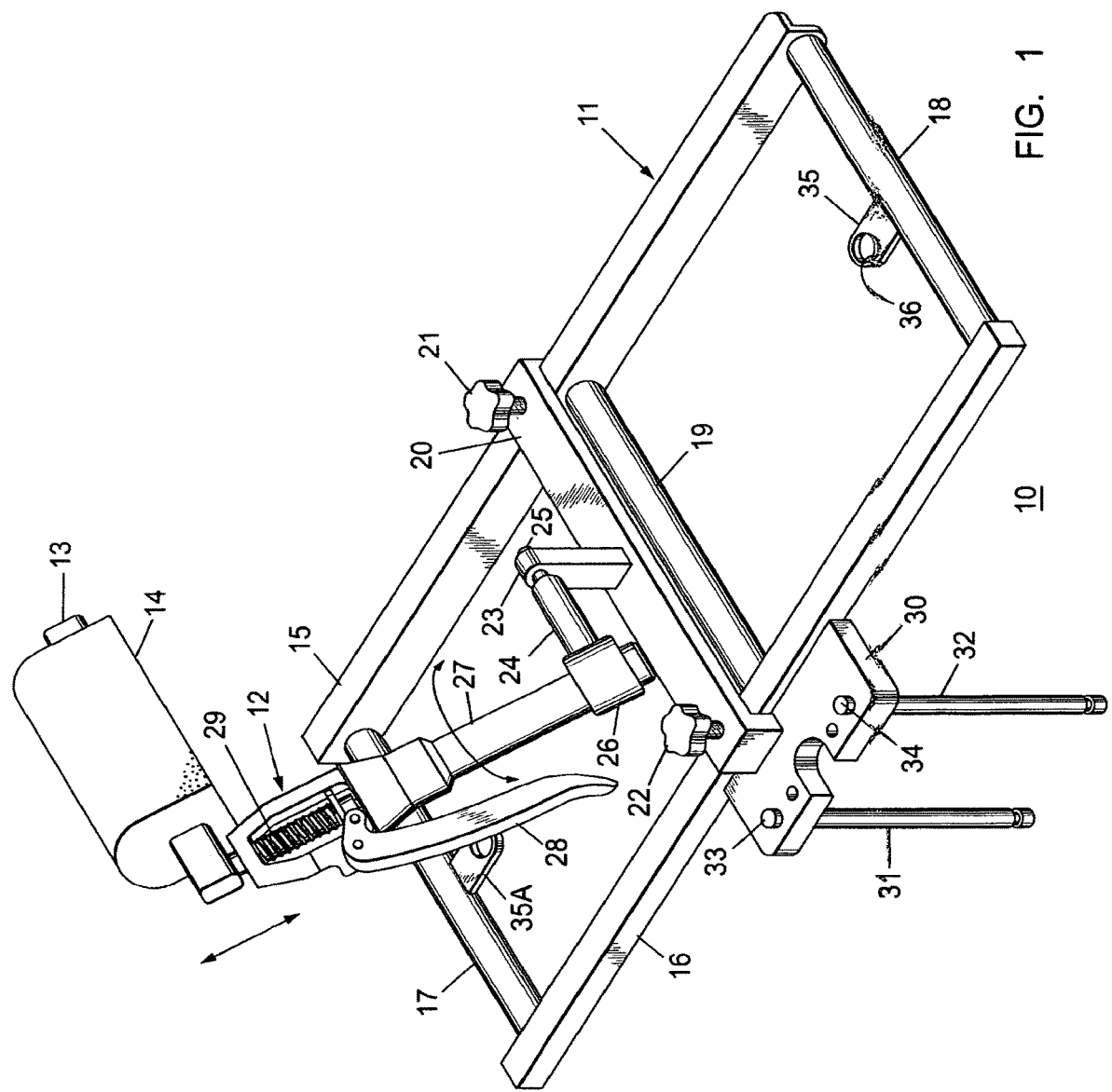
FIG. 1 is front perspective view of the modular patient's ankle distractor unit in accordance with the invention prior to attachment to the operating table.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As shown in FIG. 1, a modular ankle distractor unit 10 includes a support frame 11 and a manual distractor 12, which includes a support bar 13 for the patient support pad 14 for moving the support pad 14 in the up and down directions, as indicated, in combination with the compression spring 29 and the distractor operating handle 28. The manual distractor 12 is described within U.S. patent application Ser. No. 12/001,194 entitled "Non-Invasive Femoral Distractor," which Application is incorporated herein for purposes of reference.

Figure 2:
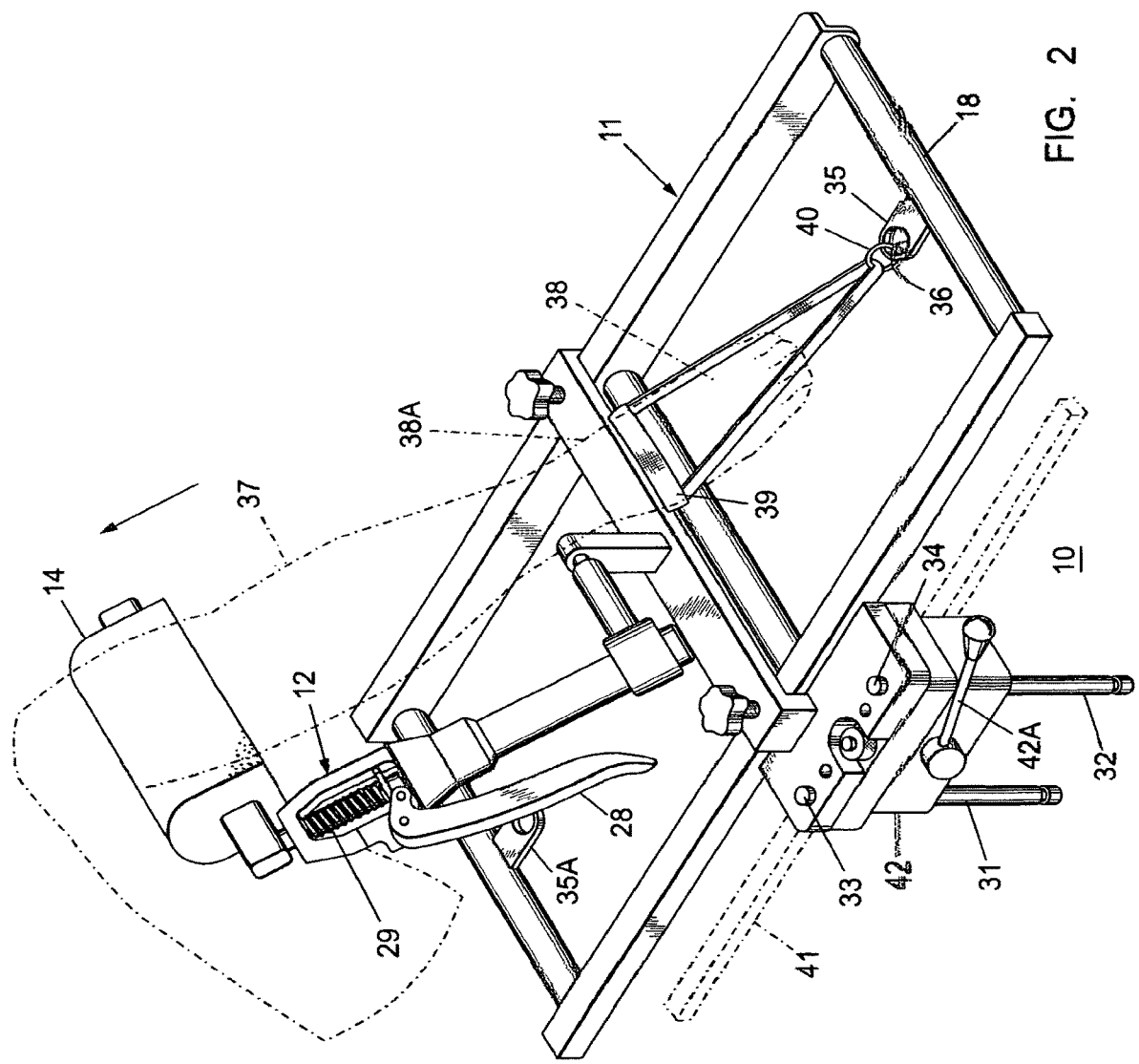
FIG. 2 is a front perspective view of the patient's ankle distractor unit of FIG. 1 after attachment to the operating table with a portion of the patient's limb depicted in phantom thereon.

The support frame 11 includes a pair of side bars 15, 16, end bars 17, 18 and center bar 19. A support bar 20 extends between the side bars 15, 16 and is attached thereto by means of threaded knobs 21 and 22. A post 23, upstanding from the support bar 20, is attached to a rod 24 by means of a bolt 25 and the rod 24 is welded to the support collar 26. One end of the manual distractor cylinder 27 is arranged within the support collar 26 whereby the manual distractor 12 can be rotated in the clockwise and counter-clockwise directions, as indicated, by loosening the bolt 25. The plate extension 30 on the end of the support bar 20 includes at a pair of operating table connector posts 31, 32 attached thereto by means of bolts 33 and 34. A tab 35 is attached to the end bar 18 and includes an opening 36 for receiving a clip connector 40 to retain the patient's foot strap 39, as shown in FIG. 2. A similar tab 35A is attached to the end bar 17.

Referring now to FIG. 2, the support frame 11 is depicted attached to an operating table side rail 41 by a side rail clamp 42 and operating handle 42A which engages the operating table connector posts 31, 32. The side rail clamp 42 is similar to that described within U.S. Pat. No. 7,380,299 entitled "Operating Table Support Clamp". To provide ankle distraction, a patient's limb 37 is arranged on the patient support pad 14 and the patient's foot 38 is secured within foot strap 39, which is secured to the end bar 18 by means of the tab 35, clip connector 40 and opening 36, as described earlier. One such foot strap 39 is a Guhl Ankle Distractor Foot Strap obtained from Smith & Nephew Inc. To provide distraction to the patient's ankle 38A, the distractor operating handle 28 on the manual distractor 12 is operated to move the patient support pad 14 and limb 37 in the indicated direction, while the ankle 38A is retained by virtue of the foot strap 39. When the distraction of the ankle 38A is completed, the compression spring 29 allows the support pad 14 to return the limb 37 to the original position upon release of the distractor operating handle 28.

A simple and efficient arrangement has been described herein whereby a patient's ankle can be precisely distracted by use of a manual distractor that is used for other limb distraction as well.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A distractor system for use in distraction surgery on a leg of a patient, comprising:
   a support collar configured to operably connect to a support frame configured to attach to a side rail of an operating table by a clamp;
   a manual distractor unit comprising a distractor body having a distractor cylinder, said distractor body configured with a support bar at one end, said support bar configured to extend transverse to said distractor body and linearly move between a first position and a second position and an adjustable assembly at an opposite end configured to operably connect said distractor cylinder to said support collar and to provide rotatable adjustment of said support bar, said support bar configured to receive a support pad thereon, said manual distractor unit further comprising a compression spring for moving said support bar to return to said first position; and
   said support collar configured to secure said distractor cylinder to said support frame while a foot strap is secured to said support frame in the distraction surgery.

2. The distractor system of claim 1, wherein said foot strap is attached at one end to said support frame during the distraction surgery.

3. The distractor system of claim 1, wherein said support pad is configured to move between said first and second positions being operably connected to said support bar using said distractor cylinder rotatably attached to said support collar and to an end bar of said support frame.

* * * * *